(12) United States Patent
Bray et al.

(10) Patent No.: US 9,278,009 B2
(45) Date of Patent: Mar. 8, 2016

(54) SPINE IMPLANTS

(75) Inventors: Robert S. Bray, Studio City, CA (US);
James M. Moran, North Royalton, OH (US); Mark T. Whiteaker, Rocky River, OH (US)

(73) Assignee: RSB SPINE LLC, Cleveland, OH (US)

( * ) Notice: Subject to any disclaimer, the term of this patent is extended or adjusted under 35 U.S.C. 154(b) by 2710 days.

(21) Appl. No.: 11/735,723

(22) Filed: Apr. 16, 2007

(65) Prior Publication Data

US 2007/0250167 A1 Oct. 25, 2007

Related U.S. Application Data

(63) Continuation-in-part of application No. 11/620,255, filed on Jan. 5, 2007, now Pat. No. 8,100,976, which is a continuation-in-part of application No. 11/248,651, filed on Oct. 12, 2005, now Pat. No. 7,985,255, which is a continuation-in-part of application No. 10/419,652, filed on Apr. 21, 2003, now Pat. No. 6,984,234.

(60) Provisional application No. 60/745,294, filed on Apr. 21, 2006.

(51) Int. Cl.
*A61F 2/44* (2006.01)
*A61B 17/86* (2006.01)
(Continued)

(52) U.S. Cl.
CPC ............. *A61F 2/4465* (2013.01); *A61F 2/4455* (2013.01); *A61B 17/86* (2013.01); *A61F 2002/2835* (2013.01); *A61F 2002/302* (2013.01); *A61F 2002/30056* (2013.01); *A61F 2002/30332* (2013.01); *A61F 2002/30433* (2013.01); *A61F 2002/30507* (2013.01); *A61F 2002/30517* (2013.01); *A61F 2002/30576* (2013.01); *A61F 2002/30578* (2013.01); *A61F 2002/30604* (2013.01); *A61F 2002/30616* (2013.01); *A61F 2002/30777* (2013.01);
(Continued)

(58) Field of Classification Search
CPC ...... A61F 2/4455; A61F 2/4465; A61F 2/447
USPC ........................................... 623/17.11–17.16
See application file for complete search history.

(56) References Cited

U.S. PATENT DOCUMENTS

| 4,904,261 | A | 2/1990 | Dove et al. |
| 5,364,399 | A | 11/1994 | Lowery et al. |

(Continued)

FOREIGN PATENT DOCUMENTS

| EP | 1103236 A2 | 11/2000 |
| EP | 1247503 A2 | 3/2002 |

(Continued)

OTHER PUBLICATIONS

Barry Chadwick and Chris Toto, "Radiolucent Structural Materials for Medical Applications", originally published MDDI Jun. 2001, 8 pages.

*Primary Examiner* — Jerry Cumberledge
(74) *Attorney, Agent, or Firm* — Cooper Legal Group, LLC

(57) ABSTRACT

An example device for the fixation and support of bone bodies includes a base member for implantation into a patient at a location between two bone bodies. The base member of the device includes an enclosed chamber for receiving fusion material and apertures for receiving bone fasteners that can be embedded into the adjacent bone bodies. The device further includes protrusions extending from the base member, wherein the protrusions are configured for engagement with one or more bone bodes upon implantation and for progressive penetration into at least one bone body over a period of time subsequent to the implantation.

50 Claims, 13 Drawing Sheets

(51) Int. Cl.
    *A61F 2/28* (2006.01)
    *A61F 2/30* (2006.01)
(52) U.S. Cl.
    CPC .......... *A61F 2002/30784* (2013.01); *A61F 2002/30841* (2013.01); *A61F 2002/449* (2013.01); *A61F 2002/4475* (2013.01); *A61F 2220/0025* (2013.01); *A61F 2220/0033* (2013.01); *A61F 2220/0041* (2013.01); *A61F 2230/0065* (2013.01); *A61F 2250/0032* (2013.01); *A61F 2310/00023* (2013.01)

(56) References Cited

U.S. PATENT DOCUMENTS

| | | | |
|---|---|---|---|
| 5,713,898 A | 2/1998 | Stucker et al. | |
| 5,713,899 A | 2/1998 | Marnay et al. | |
| 5,861,041 A * | 1/1999 | Tienboon | 623/17.16 |
| 5,865,846 A * | 2/1999 | Bryan et al. | 128/898 |
| 5,888,223 A * | 3/1999 | Bray, Jr. | 623/17.16 |
| 6,066,175 A * | 5/2000 | Henderson et al. | 623/17.11 |
| 6,159,211 A * | 12/2000 | Boriani et al. | 606/279 |
| 6,190,413 B1 * | 2/2001 | Sutcliffe | 623/17.11 |
| 6,193,721 B1 | 2/2001 | Michelson | |
| 6,231,610 B1 * | 5/2001 | Geisler | 623/17.11 |
| 6,235,059 B1 * | 5/2001 | Benezech et al. | 623/17.16 |
| 6,413,259 B1 | 7/2002 | Lyons et al. | |
| 6,432,106 B1 | 8/2002 | Fraser | |
| 6,461,359 B1 | 10/2002 | Tribus et al. | |
| 6,524,311 B2 | 2/2003 | Gaines, Jr. | |
| 6,533,786 B1 | 3/2003 | Needham et al. | |
| 6,572,622 B1 | 6/2003 | Schafer et al. | |
| 6,579,290 B1 | 6/2003 | Hardcastle et al. | |
| 6,629,998 B1 | 10/2003 | Lin | |
| 6,656,179 B1 | 12/2003 | Schaefer et al. | |
| 6,682,563 B2 * | 1/2004 | Scharf | 623/17.16 |
| 6,730,127 B2 | 5/2004 | Michelson | |
| 6,837,905 B1 * | 1/2005 | Lieberman | 623/17.16 |
| 6,884,242 B2 | 4/2005 | LeHuec et al. | |
| 6,984,234 B2 | 1/2006 | Bray | |
| 7,041,135 B2 | 5/2006 | Michelson | |
| 7,112,222 B2 * | 9/2006 | Fraser et al. | 623/17.11 |
| 7,163,561 B2 * | 1/2007 | Michelson | 623/17.16 |
| 7,232,464 B2 | 6/2007 | Mathieu et al. | |
| 7,320,708 B1 | 1/2008 | Bernstein | |
| 7,594,931 B2 * | 9/2009 | Louis et al. | 623/17.11 |
| 2002/0004683 A1 | 1/2002 | Michelson | |
| 2002/0016595 A1 | 2/2002 | Michelson | |
| 2002/0082597 A1 | 6/2002 | Fraser | |
| 2003/0167091 A1 | 9/2003 | Scharf | |
| 2003/0225409 A1 | 12/2003 | Freid et al. | |
| 2004/0127902 A1 | 7/2004 | Suzuki et al. | |
| 2004/0193269 A1 | 9/2004 | Fraser et al. | |
| 2004/0204712 A1 | 10/2004 | Kolb et al. | |
| 2004/0204713 A1 * | 10/2004 | Abdou | 606/71 |
| 2004/0236333 A1 | 11/2004 | Lin | |
| 2005/0177236 A1 | 8/2005 | Mathieu et al. | |
| 2006/0030851 A1 | 2/2006 | Bray et al. | |
| 2006/0085071 A1 | 4/2006 | Lechmann et al. | |

FOREIGN PATENT DOCUMENTS

| | | |
|---|---|---|
| JP | 2001187075 A | 7/2001 |
| JP | 2004073548 A | 3/2004 |
| WO | 9720526 | 6/1997 |
| WO | 9856319 | 12/1998 |
| WO | WO 9858604 | 12/1998 |
| WO | 9927864 A2 | 6/1999 |
| WO | 0007527 | 2/2000 |
| WO | 0066011 A1 | 11/2000 |
| WO | 0066045 | 11/2000 |
| WO | 0180785 A1 | 11/2001 |
| WO | 0195837 | 12/2001 |
| WO | 0203885 A2 | 1/2002 |
| WO | WO 03005938 | 1/2003 |
| WO | WO 2004069106 | 8/2004 |
| WO | 2004093654 A | 11/2004 |
| WO | 2005117767 A2 | 12/2005 |

* cited by examiner

SPINE IMPLANTS

RELATED PATENT APPLICATION

This application claims the benefit of, as a non-provisional application of, U.S. Provisional Patent Application No. 60/745,294 filed Apr. 21, 2006, and claims the benefit of, as a continuation-in-part application of, U.S. patent application Ser. No. 11/620,255 filed Jan. 5, 2007, now U.S. Pat. No. 8,100,976, and, as a continuation-in-part application of, U.S. patent application Ser. No. 11/248,651 filed Oct. 12, 2005, now U.S. Pat. No. 7,985,255, both of which claim benefit of and are continuations-in-part applications of U.S. patent application Ser. No. 10/419,652 filed Apr. 21, 2003, now U.S. Pat. No. 6,984,234, the contents of all of which are incorporated herein by reference in their entirety.

FIELD OF THE INVENTION

The present invention relates generally to implant devices for the fixation and support of bone bodies. In particular, the present invention relates to an implant device that provides and controls limited movement between bone bodies during fusion.

BACKGROUND OF THE INVENTION

The spinal column of vertebrates provides support to bear weight and protection to the delicate spinal cord and spinal nerves. The spinal column includes a series of vertebrae stacked on top of each other. There are typically seven cervical (neck), twelve thoracic (chest), and five lumbar (low back) segments. Each vertebra has a cylindrical shaped vertebral body in the anterior portion of the spine with an arch of bone to the posterior, which covers the neural structures. Between each vertebral body is an intervertebral disc, a cartilaginous cushion to help absorb impact and dampen compressive forces on the spine. To the posterior the laminar arch covers the neural structures of the spinal cord and nerves for protection. At the junction of the arch and posterior vertebral body are articulations to allow movement of the spine.

Various types of problems can affect the structure and function of the spinal column. These can be based on degenerative conditions of the intervertebral disc or the articulating joints, traumatic disruption of the disc, bone or ligaments supporting the spine, tumor or infection. In addition congenital or acquired deformities can cause abnormal angulation or slippage of the spine. Slippage (spondylolisthesis) anterior of one vertebral body on another can cause compression of the spinal cord or nerves. Patients who suffer from one of more of these conditions often experience extreme and debilitating pain, and can sustain permanent neurological damage if the conditions are not treated appropriately.

One technique of treating these disorders is known as surgical arthrodesis of the spine. This can be accomplished by removing the intervertebral disc and replacing it with bone and immobilizing the spine to allow the eventual fusion or growth of the bone material across the disc space to connect the adjoining vertebral bodies together. The stabilization of the vertebra to allow fusion is often assisted by a surgically implanted device to hold the vertebral bodies in proper alignment and allow the bone to heal, much like placing a cast on a fractured bone. Such techniques have been effectively used to treat the above-described conditions and in most cases are effective at reducing the patient's pain and preventing neurological loss of function. However, there are disadvantages to the present stabilization devices.

Several types of anterior spinal fixation devices are in use currently. One technique involves placement of screws all the way through the vertebral body, called bicortical purchase. The screws are placed through a titanium plate but are not attached to the plate. This device is difficult to place, and over penetration of the screws can result in damage to the spinal cord. The screws can back out of the plate into the surrounding tissues, as they do not fix to the plate. Several newer generation devices have used a unicortical purchase of the bone, and in some fashion locking the screw to the plate to provide stability and secure the screw from back out. Problems have resulted from over rigid fixation and stress shielding, resulting in nonunion of the bony fusion, chronic micromotion during healing resulting in stress fracture of the fixation device at either the screw or the plate, insecure locking of the screw to the plate resulting in screw back out, or inadequate fixation strength and resultant collapse of the graft and angulation of the spine.

These devices are often designed to support and bridge across a group of vertebrae, for example a group of three. Because these devices are typically bridged across the bone, for example in the cervical region, they occasionally aggravate the esophagus, making it difficult for one to swallow food. In addition, the screws are installed into the bone normal, i.e., 90° to the plate's surface. Local angularity in the vertebral column often causes high shearing stresses to be applied to the screws. These stresses may fatigue the screws or cause deformation of the screw holes.

BRIEF SUMMARY OF THE INVENTION

The following presents a simplified summary of the invention in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

In accordance with an aspect of the present invention, an implant device is provided. The device includes a base member configured to interface with two or more bone bodies. The base member includes a primary member that forms a peripherally-surrounded bone chamber for receiving fusion material and a secondary member that extends at an angle relative to the primary member. A plurality of interface members extend from a surface of the base member. The interface members are configured to provide controlled subsidence of the device into at least one bone body. The device further includes a plurality of bone fasteners that extend through apertures provided in the base member.

In accordance with another aspect of the present invention, an implant device is provided. The device includes a base member that includes a peripherally-surrounded chamber for receiving fusion material. The peripherally-surrounded chamber has a top surface and a bottom surface. The device has a plurality of bone fasteners extending through apertures provided in the base member. The device includes restraining means for restricting movement of at least one bone fastener. The device includes at least one interface member extending from a surface of the peripherally-surrounded chamber. The interface member is configured to provide controlled subsidence of the device into a bone body.

In accordance with yet another aspect of the present invention, an implant device is provided. The device includes a base member configured to interface with first and second adjacent bone bodies. The base member includes a primary member that forms a peripherally-surrounded bone chamber for receiving fusion material and configured such that the first and second bone bodies engage the fusion material for permitting force transmission between the first and second bone bodies through the fusion material. The device includes means for controlled subsidence of movement of the first and second bone bodies toward each other.

The following description and the annexed drawings set forth in detail certain illustrative aspects of the invention. These aspects are indicative, however, of but a few of the various ways in which the principles of the invention may be employed and the present invention is intended to include all such aspects and their equivalents. Other objects, advantages and novel features of the invention will become apparent from the following detailed description of the invention when considered in conjunction with the drawings.

BRIEF DESCRIPTION OF THE DRAWINGS

The foregoing and other features and advantages of the present invention will become apparent to those skilled in the art to which the present invention relates upon reading the following description with reference to the accompanying drawings.

DESCRIPTION OF EXAMPLE EMBODIMENTS

Figure 1:
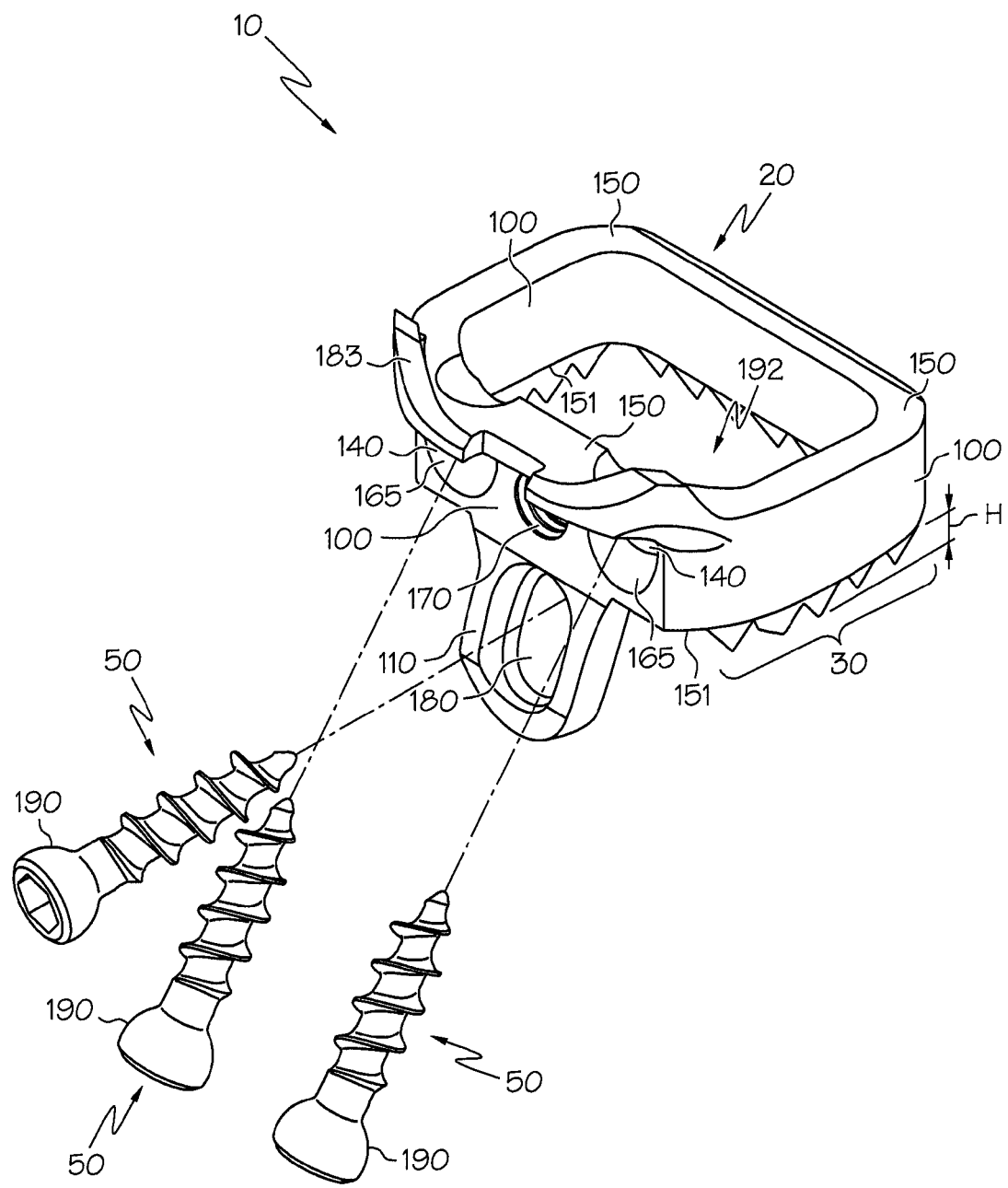
FIG. 1 is an angled front perspective view of an implant device including a base member having a peripherally-surrounded chamber in accordance with an aspect of the present invention.

The present invention relates to a device, such as an implant device that provides and controls limited movement between bone bodies during fusion. The present invention will now be described with reference to the drawings, wherein like reference numerals are used to refer to similar elements throughout. It is to be appreciated that the various drawings are not necessarily drawn to scale from one figure to another nor inside a given figure, and in particular that the size of the components are arbitrarily drawn for facilitating the understanding of the drawings. In the following description, for purposes of explanation, numerous specific details are set forth in order to provide a thorough understanding of the present invention. It may be evident, however, that the present invention can be practiced without these specific details. Additionally, other embodiments of the invention are possible and the invention is capable of being practiced and carried out in ways other than as described. The terminology and phraseology used in describing the invention is employed for the purpose of promoting an understanding of the invention and should not be taken as limiting.

Referring initially to FIG. 1, an example of a device or implant device 10 is illustrated in accordance with an aspect of the present invention. The implant device 10 is configured to fix and secure two or more bone bodies. As used herein, the phrase "bone bodies" is intended to include individual bones as well as fragments or portions of bones. For example, the bone bodies can be two adjacent vertebrae and the implant device 10 can be mounted to the vertebrae with graft material (not shown) between the vertebrae. More specifically, and as will be described in further detail below, the implant device 10 can fix and secure adjacent vertebrae that have had cartilaginous disc between the vertebrae replaced with material that promotes the fusion of the vertebrae such as a graft of bone tissue or some other similar material. It is to be appreciated that one aspect that is addressed by the present invention is load sharing with a graft.

As shown in FIG. 1, the configuration of the implant device 10 includes a base member 20 having a plurality of protrusions or interface members 30 extending from a surface of the base member 20. The base member 20 has a top surface 150 and a bottom surface 151. As shown, the interface members 30 extend from the bottom surface 151 of the base member 20. Although not shown, the interface members 30 can alternatively extend from only the top surface 150 of the base member 20, or from both the top surface 150 and the bottom surface of the base member 20 in order to provide two controlled subsidence interfaces between the implant device 10 and adjacent bone bodies. The interface members 30 are configured to contact at least one surface of a bone body to provide subsidence control for the implant device 10. The interface members 30 can include, for example, teeth, knife-edges, spikes, posts, pegs, or combinations thereof.

The base member 20 is configured such that when first inserted between two adjacent bone bodies, the interface members 30 contact a surface of at least one of the bone bodies. The interface members 30 are configured such that substantially immediate penetration into a bone body occurs. The implant device 10 gradually subsides as the bone bodies and bone graft fuse to share in the weight bearing during settling of the bone or vertebral bodies. Specifically, as the bone bodies move toward each other during settling, the interface members 30 will penetrate the bone bodies with increased resistance to subsidence.

Controlled subsidence relates to resistance to subsidence and total amount of subsidence. To promote controlled subsidence, the interface members 30 may extend from a surface of the base member in a direction that is aligned with an elongate direction of two adjacent bone bodies, such as two vertebrae in a spine. The interface members are thus configured to provide progressive penetration into a bone body over a period of time. The subsidence profile, which is a relationship between an applied load and an amount of settling the implant device 10 experiences when secured to the bone bodies, is dependent on the configuration or shape of the interface members 30. For example, the interface members 30 can readily penetrate into a bone body initially and then slow down as more of the interface member cross section embeds. The height (H) of the interface members 30 relative to the depth of penetration into a corresponding bone body. Generally, when the implant device 10 has subsided to a point where the interface members are fully embedded in the bone, the applied load will be distributed across the entire surface of the implant device 10 and subsidence resistance will increase. The controlled subsidence relationship between the interface members 30 and the at least one corresponding bone body that the members 30 extend into is described in U.S. patent application Ser. No. 11/248,651, which is incorporated herein by reference in its entirety.

The base member 20 of the implant device 10 includes a primary member 100 and a secondary member 110, which extends from and is angled relative to the primary member 100. The primary member 100 forms an enclosed loop or peripherally-surrounded chamber 192 that is configured to receive and hold fusion material, such as a bone graft. As shown, the chamber 192 is peripherally-surrounded, but not fully enclosed, such that bone bodies residing above and below the chambers 192 can be in contact with fusion material located in the chamber 192. It is to be appreciated, and for the description purposes of the present invention herein, the peripherally-surrounded chamber 192 can be positioned at any angle in order to accommodate the orientation of bone bodies to be fused together. In any case, the chamber 192 can mitigate lateral shift of the fusion material and control subsidence of adjacent bone bodies as they set during fusion. Subsidence is further controlled by the presence of the interface members 30 that extend from a surface of the base member 20. In the present embodiment, the primary and secondary members 100, 110 are contiguous and unitary. The secondary member 110 has a front surface that is generally continuous with a front surface of the primary member 100, and a back surface that is generally continuous with a back surface of the primary member 100. The primary member 100 and secondary member 110 are arranged relative to each other so that their front surfaces form an angle. Of course, the angle is not of great importance and typically depends upon a compromise between low profile and the amount of bone that would need to be removed. Suffice to say that the angle can be any angle (e.g., greater than 90° and less than 180°). However, a typical angle would be in the range, from about 140° to about 170°. The angle at which the primary and secondary members 100, 110 are joined is provided so that bone screws can be introduced through the base member 20 at desired angles. Alternatively, the base member 20 can be designed in any other manner that permits the bone screws to be introduced there through at the desired angles.

The primary member 100 can form the peripherally-surrounded chamber 192 to be of any shape or size to accommodate adjacent bone bodies of various shapes, sizes and positions. The peripherally-surrounded chamber 192 of the present invention is designed to have an outer periphery that coincides with or generally matches the outer diameter of the cortex or adjacent vertebrae. The top surfaces of the implant device 10 sit at, and preferably below, the top surface of the vertebral bodies. As such, the implant device 10 of the present invention does not have any parts that would significantly interfere with or irritate the adjacent anatomic structures of the patient. As shown, the peripherally-surrounded chamber 192 has a rounded-edge rectangular shape that would adequately accommodate two adjacent vertebrae of a spinal column. The primary member 100 generally forms the vertically-open and peripherally-surrounded area 192, when viewed in the implanted position in a spinal column, that can receive and hold fusion material between two or more bone bodies. In use, the primary member 100 laterally extends around an amount of fusion material, such as a bone graft, in order to mitigate lateral shift of the graft and control subsidence of adjacent vertebrae as the vertebrae set during fusion. The fusion material can be packed into the peripherally-surrounded chamber 192 formed by the primary member 100. The chamber 192 of the implant device 10 creates a one-piece fusion material housing that substantially reduces the need for other devices that may be necessary to fuse multiple bone bodies together. The peripherally-surrounded chamber 192 adequately houses fusion material that would generally be supported by a cage design implant. In this case, a plate would generally also be needed to keep the bone bodies and the cage in the desired location. The implant device 10 described herein significantly reduces the cost associated with multiple-device fusion methods such as those associated with the above cage and plate combination devices.

Another advantage of the implant device 10 is that it is stackable. The implant device 10 of the present invention covers an insignificant portion of the top surfaces of the vertebral bodies to which it is attached. As a result, multiple implant devices can be introduced over adjacent bone grafts (i.e., between a common vertebral body) so that two implant devices 10 are attached to a common vertebral body without devices 10 contacting one another. Thus, subsequent procedures where new bone grafts are to be inserted do not require the removal of a pre-existing device prior to introduction of a new device. The depicted systems where the bone screws are provided in a generally triangular arrangement further enhance the stacking ability of the implant devices 10 of the invention. It is to be appreciated that the implant device 10 can be of different scales or sizes, have differing bone screw lengths and restraining plates that are complementary to different physical dimensions of the patients on whom the invention is used and the spinal location or level at which the device is implanted. The present invention is capable of being provided in various sizes for that purpose.

The peripherally-surrounded chamber area 192 provides a retaining region or open area into which fusion material can be packed or loaded. It is possible to load fusion material, such as particulate graft material including bone chips and/or bone paste, into the chamber 192 prior to the insertion of the implant device 10 between adjacent bone bodies such as vertebrae. Bone chips and/or bone paste and possibly in combination with growth factors can be used in place of a block of bone graft material. Often it is the case that bone chips and bone paste are more easily retained in a peripherally-surrounded chamber 192 as opposed to an implant device 10 which has an open posterior end. Thus, a combination of bone chips and bone paste is better retained in a center region of an implant device 10 such as that provided in the Figures shown herein.

In accordance with another aspect of the present invention, any portion or the entire implant device 10 can be constructed from radiotransparent or radiolucent materials. Specifically, in order to facilitate radiographic evaluation of the fusion material and the corresponding bone bodies, the base member 20, primary member 100, secondary member 110, any other portion or component of the implant device 10 or combinations thereof can be constructed from radiotransparent or radiolucent materials. For example, the entire implant device 10 can be constructed from radiolucent material. Radiolucent materials permit x-rays to pass through components of the implant device 10 so that developed x-ray pictures provide more visibility of the fusion material and bone bodies without significant interference, such as imaging artifacts, caused by the device 10. Radiolucent materials enable clear visualization through imaging techniques such as x-ray and computer tomography (CT), whereas traditional metallic or alloy implant materials that are radiopaque can generate imaging artifacts and scatter that prevent a comprehensive inspection of the surrounding tissue, bone and fusion material. Thus, radiolucent materials allow for clearer imaging of bone bodies and fusion materials.

Radiolucent materials can include, but are not limited to, polymers, carbon composites, fiber-reinforced polymers, plastics, combinations thereof and the like. One example of a radiolucent material that can be used with the aspects of the present invention described herein is PEEK-OPTIMA® polymer supplied by Invibio Inc., Greenville, S.C. The PEEK-OPTIMA® polymer is a polyaromatic semicrystalline thermoplastic known generically as pplyetheretherketone. The PEEK-OPTIMA® polymer is a biocompatible and inert material. Known alternatives to PEEK-OPTIMA® include, but are not limited to, biocompatible polymers such as ENDOLIGN® polymer composite supplied by Invibio Inc., Greenville, S.C. The ENDOLIGN® polymer is a biocompatible carbon fiber-reinforced thermoplastic material. Radiolucent materials, including those described above, can optionally be doped or combined with radiopaque materials in different concentrations in order to vary the level of x-ray contrast and/or visual characteristics. The portions of the implant device 10 constructed from radiolucent material can be prepared by any conventional technique known in the art such as machining, injection molding or compression molding.

Figure 4:
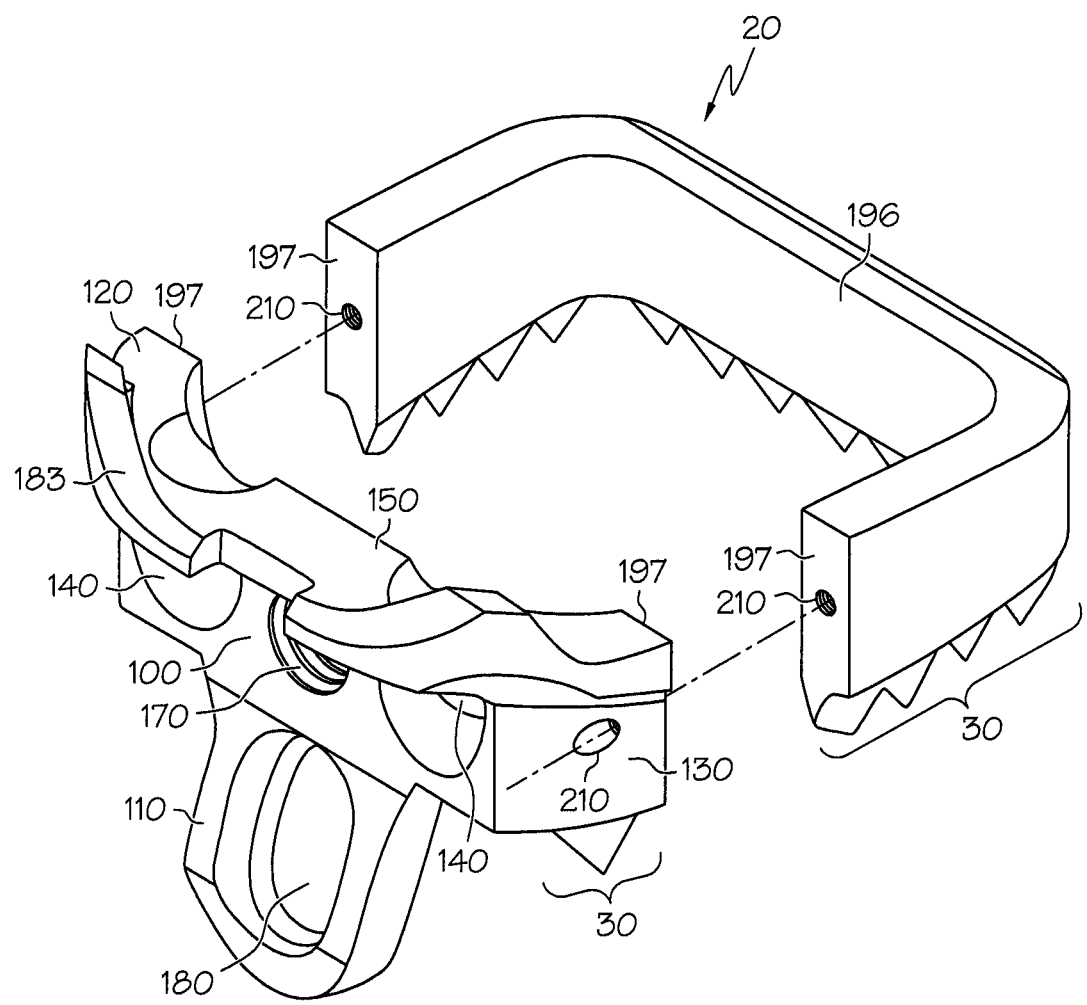
FIG. 4 is an angled front perspective view of a base member of an implant device including a peripherally-surrounded, chamber in the unassembled position in accordance with an aspect of the present invention.

In another embodiment, the implant device 10 can include a combination of components constructed from both radiolucent materials and radiopaque materials. Radiopaque materials are traditionally used to construct devices for use in the medical device industry. Radiopaque materials include, but are not limited to, metal, aluminum, stainless steel, titanium, titanium alloys, cobalt chrome alloys, combinations thereof and the like. Radiopaque materials tend to obstruct x-rays and thus restrict x-ray visibility to the regions in which the materials are located. However, radiopaque materials generally have structural characteristics that are advantageous with regard to medical devices. That is, some radiolucent materials lack the strength and/or rigidity of radiopaque materials and certain design modifications may be made to provide adequate structural integrity of the implant device 10. Radiopaque materials generally have increased rigidity as compared to radiolucent materials and thus radiopaque materials may tend to maintain bone body alignment despite the rigorous pressures and forces generated by a patient implanted with the implant device 10. Thus, it may be desirable to construct portions of the implant device 10 from radiopaque materials such as metal and other portions of the implant device 10 from radiolucent materials so that a desired level of strength and/or rigidity is obtained and also x-ray visibility is enhanced. For example, as shown in FIG. 4, the chamber member 196 connected to the first and second legs 120, 130 of the primary member 100 can be constructed from radiolucent material in order to enhance the x-ray visibility of the fusion material located in the peripherally-enclosed area formed by the chamber member 196 and first and second legs 120, 130 of the primary member 100 and the surrounding bone bodies. However, it is to be appreciated that radiopaque material may be used in otherwise radiolucent devices for other reasons. For example, devices that are primarily radiolucent may include radiopaque markers such that the location of the device may be readily ascertained.

The base member 20 of the implant device 10 can include a plurality of apertures, each of which is configured to receive a corresponding bone fastener 50 there through. The bone fastener 50 can include a bone screw, a plurality of which is used for securing the implant device 10 to adjacent bone bodies. The bone fasteners 50 can be made of any suitable material, such as titanium or a titanium alloy, a radiolucent material, a radiopaque material, or combinations thereof. The plurality of bone fasteners 50 can all have the same shape, such as that shown in FIGS. 1 and 2. In the depicted examples, the bone fasteners each have a radiused head 190. As used herein, the term "radiused head" means that the lower portion of the bone screw head, i.e., the portion that is nearest the shank, is generally rounded, to thereby permit the bone screws to toggle within their respective holes 140 and slots 180.

In another embodiment, the bone screws 50 configured to pass through the apertures in the base member 20 can have pointed ends which include a cutting flute on the tip. The cutting flute at the tip of the bone screw 50 allows the screw to be self-drilling or self-tapping. Thus, the use of a bone screw 50 having a self-drilling or self-tapping tip makes the use of a drill or center punch optional.

For an enhanced fit of the implant device 10, a portion of bone can be trimmed or otherwise removed from a lip osteophyte of a bone body at an angle corresponding to bone screw holes 140, 180. The angles of the bone screws 50 relative to the bone surfaces of the bone bodies can affect the anchoring of bone screws 50. For example, the lip osteophyte is the strongest part of a vertebra, and thus angling the bone screws 50 through the lip osteophyte increases the ability of the base member 20 to stay anchored to the vertebral bodies. By being angled, each bone screw 50 is positioned along an angle of rotation of a corresponding bone body as well as an angle of settling of the bone body. This configuration places each screw 50 in a protected position against motion of the spinal column. As a result, significant shear forces are not exerted on the screws 50 as the vertebral bodies rotate and/or settle.

The primary member 100 includes at least one, and preferably two as shown, first bone screw holes 140 extending there through, each being configured to receive a corresponding bone fastener or screw 50. The first bone screw holes 140 in the primary member 100 are located on the front face of the primary member 100 and face outward from the patient when the implant device 10 is inserted. The bone screw holes 140 are configured such that the bone screws 50 extend through the holes 140 at an angle. As a result, each bone screw extending through the first bone screw holes 140 can enter the bone body at an angle. Each of the first bone screw holes 140 is sufficiently large to allow a portion of a respective bone screw 50 to pass there through but not large enough to allow a retaining portion of the bone screw through, such as the head 190 of the bone screw. Further, each of the first bone screw holes 140 has a seat 165 on which the retaining portion of a respective bone screw rests. Each seat 165 has a generally concave spherical shape and the surface of the retaining portion of the bone screw 50 in contact with the seat 165 has a complementary convex spherical configuration. Consequently, the bone screws 50 are free to pivot on the seats 165. The primary member 100 also includes a threaded hole 170 for receiving a restraining means configured to mitigate the backing out of at least one bone fastener from a bone body.

The secondary member 110 includes a second bone screw hole 180 in the form of an elongated slot for receiving a bone screw. The bone screw is introduced into the second bone screw hole 180 and into a second bone body. The second bone screw hole 180 is configured such that a bone screw can slide and rotate within the slot relative to the base member 20 and generally toward the primary member 100. Thus, in use, as two adjacent bone bodies, to which the base member 20 is fixed, collapse or settle and move toward each other, the bone screw contained within the second bone screw hole 180 will slide within the slot and move with the bone body into which it extends in a direction toward the primary member 100 and the other bone body. It is worth noting that since the slot is at an angle to the surface features, it is actually longer in the plane of the secondary member than the surface features are tall. In other words, the slot provides screw movement in the vertical direction equivalent to the height of the surface features.

At least one and preferably two projections 183 extend upwardly from the top surface 150 of the base member 20. The projections 183 contact a surface of the bone bodies to provide a stop when inserting the base member 20 between the bone bodies. The projection 183 provides a base or shelf that contacts a bone body in order to stop the implant device 10 against a corresponding bone body upon insertion into a patient. Although not shown in FIG. 1, the at least one projection 183 can alternatively be positioned to extend from the bottom surface of the primary member 100.

Figure 2:
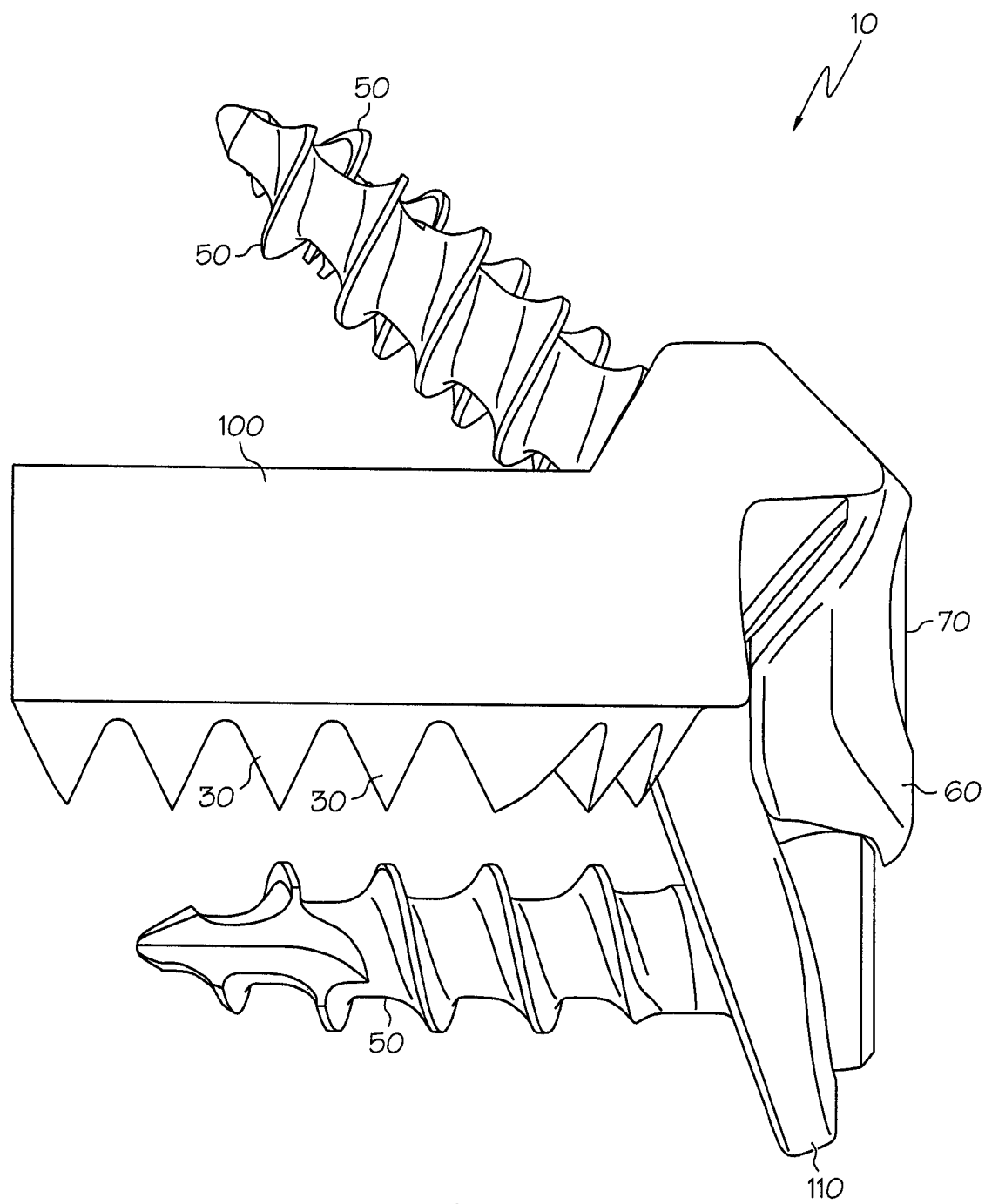
FIG. 2 is a side view of an implant device in accordance with an aspect of the present invention.

As shown in FIG. 2, the implant device 10 may include restraining means for restricting movement of one or more bone fasteners 50 coupled to the base member 20. The restraining means may be any means for securely covering at least a portion of at least one bone fastener 50 so that the bone fastener 50 is prevented from backing out of a bone body once screwed in. In the depicted embodiment, the bone screw restraining means includes a restraining plate 60 and a restraining plate fixing means 70, such as a screw that can be configured to fit into hole 170. As such, the restraining plate 60 could merely be a cover plate. The restraining plate 60 may be made of any suitable material known in the art, such as titanium or a titanium alloy, a radiolucent material, a radiopaque material, or combinations thereof. The restraining means does not have to be permanently fixed to the base member and may be removable. In the shown example, the restraining plate 60 is configured to correspond with a recessed region of the base member 20. The recessed region facilitates proper positioning of the restraining plate 60. The thickness of the restraining plate 60 should generally be as thin as possible, for example in the range from about 0.5 mm to about 2 mm. Alternative example embodiments of the restraining plate 60 and the way the embodiments interface with the bone fasteners are illustrated and described in U.S. patent application Ser. No. 11/620,255, which is incorporated herein by reference in its entirety. Also, the restriction of movement of one or more bone fasteners provided by restraining means may include control of relative motion (i.e., resistance to relative motion or changing resistance to relative motion) between one or bone fasteners and the base plate during subsidence. Still further, it is to be appreciated that within yet another example the restriction of movement as provided by restraining means may be considered to include both (1) bone fastener back-out prevention and (2) control of relative motion between one or bone fasteners and the base plate during subsidence.

Additionally, it is to be appreciated that any other suitable bone screw restraining means can be used in connection with the present invention. For example, the bone screw restraining means can include multiple restraining plates that cover different bone screws. Alternatively, the bone screw restraining means can include one or more screws with heads that overlap at least a portion of one or more bone screws to thereby prevent the bone screws from backing out.

In another embodiment, the peripherally-surrounded chamber 192 formed by the primary member 100 can be divided into multiple interior compartments by interior members. Interior members can be composed or radiolucent or radiopaque materials. In order to increase radiographic evaluation of adjacent bone bodies and fusion material contained in each compartment of the peripherally-surrounded chamber 192, the interior members are preferably composed of radiolucent material. The peripherally-surrounded chamber 192 has a substantially flat inner face surface formed by the primary member 100. As illustrated, the interface members 30 can extend from the bottom surface of the peripherally-surrounded chamber 192 in order to provide controlled subsidence with an adjacent bone body. Although not shown, the interface members can alternatively extend from the top surface of the peripherally-surrounded chamber 192 or from both the top and bottom surfaces of the chamber 192.

Figure 3:
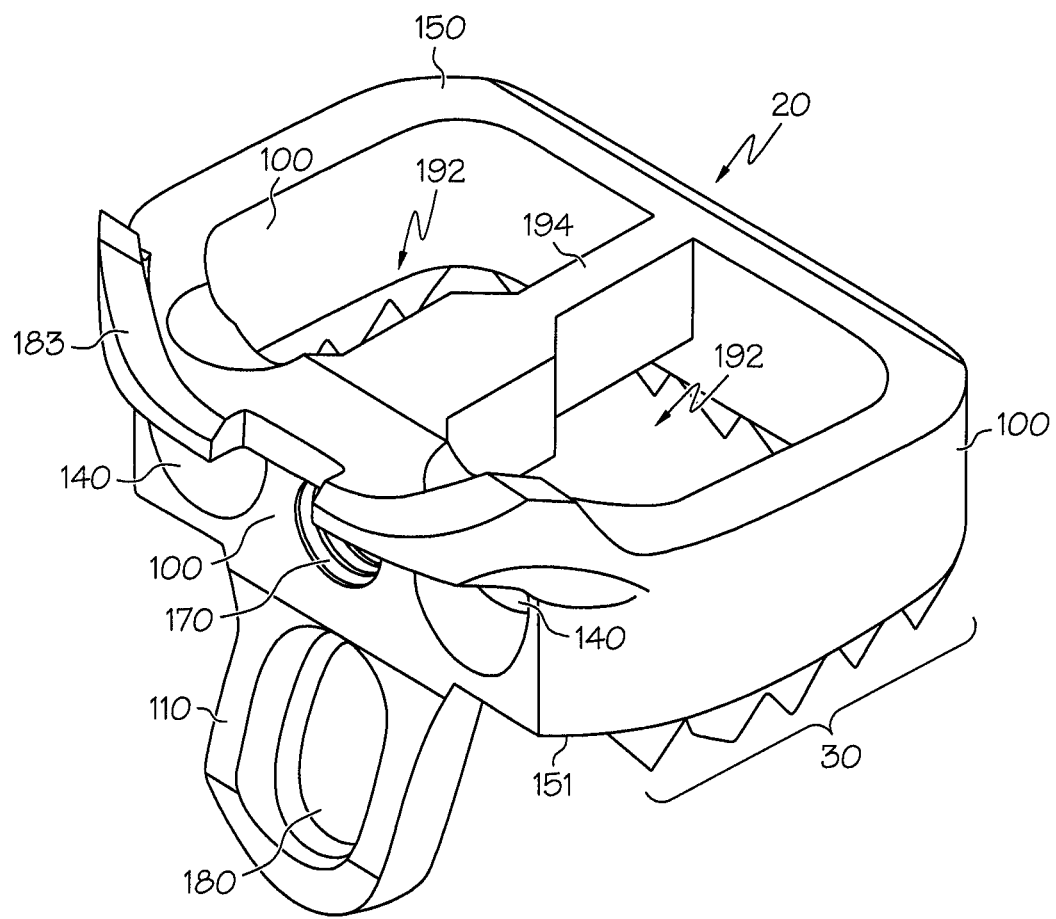
FIG. 3 is an angled front perspective view of a base member of an implant device including a peripherally-surrounded, multiple-compartment chamber in accordance with an aspect of the present invention.

As shown in FIG. 3, a center interior member 194 can extend between the opposing inner surface faces of the chamber 192 such that the chamber 192 is divided into two or more compartments that can each hold or house fusion material to be placed between two adjacent bone bodies. As illustrated, the interior member 194 of FIG. 3 extends from a portion of the inner face of the peripherally-surrounded chamber 192 and is connected to an opposing inner face of the chamber 192 or primary member 100. The addition of interior members, such as member 194, in the peripherally-surrounded chamber 192 can add overall support and strength to the implant device 10. Interior members can further secure the fusion material between two bone bodies. It should be appreciated that one possible benefit associated with the presence of the interior member 194 is that it helps prevent PEEK implants from fracturing if they are impacted between the bones with excessive force.

It is possible to load fusion material such as bone paste or bone chips into the peripherally-surrounded chamber 192 prior to insertion of the implant device 10 between adjacent bone bodies (e.g., vertebrae). However, it may be easier to insert a chamber member having an open anterior face between adjacent bone bodies. In this case, the chamber member can then be packed with fusion material from the anterior face and then sealed off with a plate, such as the base member 20. Along this line, in order to ease the packing of the peripherally-surrounded chamber 192 and the overall insertion of the implant device 10 into a patient, it may be desirable to detach the chamber member 196 which forms a portion of the peripherally-surrounded chamber 192 from the primary member 100. In accordance with another aspect of the present invention, FIG. 4 illustrates that the primary member 100 can include a detachable chamber member 196 that encloses the open area or peripherally-surrounded chamber 192 that is configured to receive fusion material. The primary member 100 can further include a first leg 120 and a second leg 130 that form a curved open arc for receiving fusion material. As illustrated, the first and second legs 120, 130 of the primary member 100 can form generally a U-shape. The detachable function of the chamber member 196 allows the U-shaped open area formed by the first and second legs 120, 130 of the primary member 100 and the U-shaped chamber member 196 itself to be packed with fusion material separately before being subsequently implanted between two adjacent bone bodies.

The chamber member 196 can be constructed from radiolucent material or radiopaque material. Because the chamber member 196 can potentially limit radiographic evaluation of the fusion material and adjacent bone bodies, it may be desirable to construct the chamber member 196 from radiolucent material. As shown, the chamber member 196 has a U-shape. However, the chamber member 196 can have any shape or be configured to match the shape of an adjacent bone body. When the chamber member 196 is connected with the first and second legs 120, 130 of the primary member 100, the peripherally-surrounded chamber 192, as shown, is generally rectangular. Although not shown, the peripherally-surrounded chamber 192 can be circular or any other desirable shape depending on the configuration of the chamber member 196 and first and second legs 120, 130. The chamber member 196 further has a top surface and a bottom surface that corresponds and aligns with the top 150 and bottom 151 surfaces of the primary member 100.

As shown in FIG. 4, the chamber member 196 can be connected to the first and second legs 120, 130 of the primary member 100 by a fastener, such as a screw or dowel, which can be inserted in the illustrated attachment holes 210. The attachment holes 210 extend through the first and second legs 120, 130 of the primary member 100 and are designed to be in register with the corresponding attachment holes 210 in the chamber member 196 when the implant device 10 is assembly such that the chamber member 196 is attached or fastened to the primary member 100 in order to form the peripherally-surrounded chamber 192. The attachment face 197 of the first and second legs 120, 130 is substantially flat such that it fits flush with the attachment face 197 of the chamber member 196. Thus, when the first and second legs 120, 130 are fastened to the chamber member 196, the attachment faces 197 are in register and the chamber member 196 is tightly secured to the primary member 100.

Figure 5:
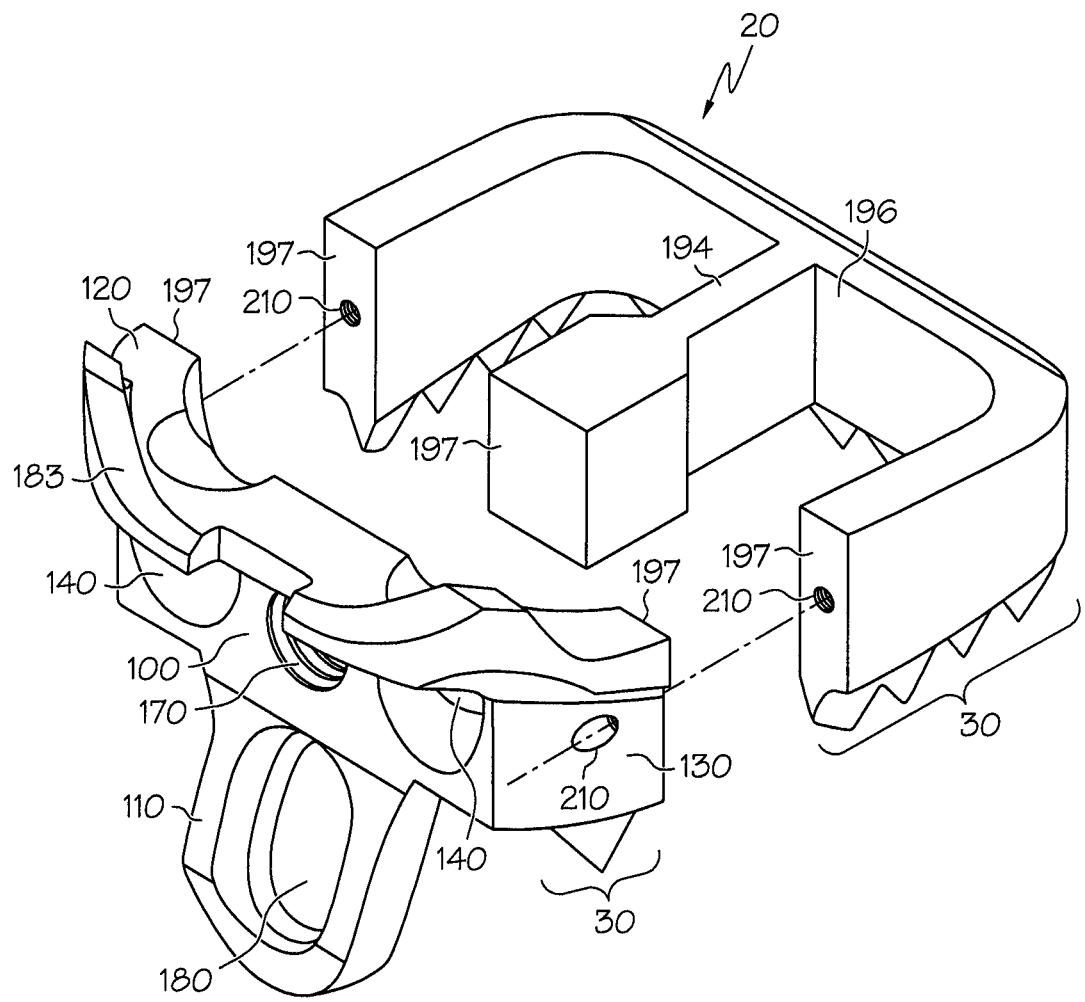
FIG. 5 is an angled front perspective view of a base member of an implant device including a laterally-enclosable, multiple-compartment chamber in an unassembled position in accordance with an aspect of the present invention.

It is to be appreciated that the peripherally-surrounded chamber 192 can be divided into more than one interior compartment if desired, such as that shown in FIG. 5, for example. FIG. 5 illustrates a U-shaped detachable chamber member 196 having an interior member 194 extending outwardly from the inner face of the chamber member 196 in a direction parallel with the ends of the chamber member 196 having the attachment faces 197. The primary member 100 and chamber member 196 can be coupled together by any suitable structure or conventional means known in the art. As shown, the interior member 194 has an attachment face 197 that is substantially flat. The attachment face 197 of the interior member 194 is designed to align and fit flush with a portion of the surface of the primary member 100. Although not shown, the attachment face 197 of the interior member 194 can include a threaded fastener hole. The hole 170 could be configured differently, e.g., as a clearance hole, such that the restraining means can extend into the fastener hole of the interior member 194. In this case, the fastener used to attach the restraining means to the base member 20 can extend into the interior member 194 in order to secure the detachable chamber member 196 to the primary member 100. Similarly as shown in FIG. 4, the attachment faces 197 of the chamber member 196 and first and second legs 120, 130 can include attachment holes 210 for fastening the two together. A screw, dowel or like fastener can be used to secure the chamber member 196 to the first and second legs 120, 130 of the primary member 100.

Figure 6:
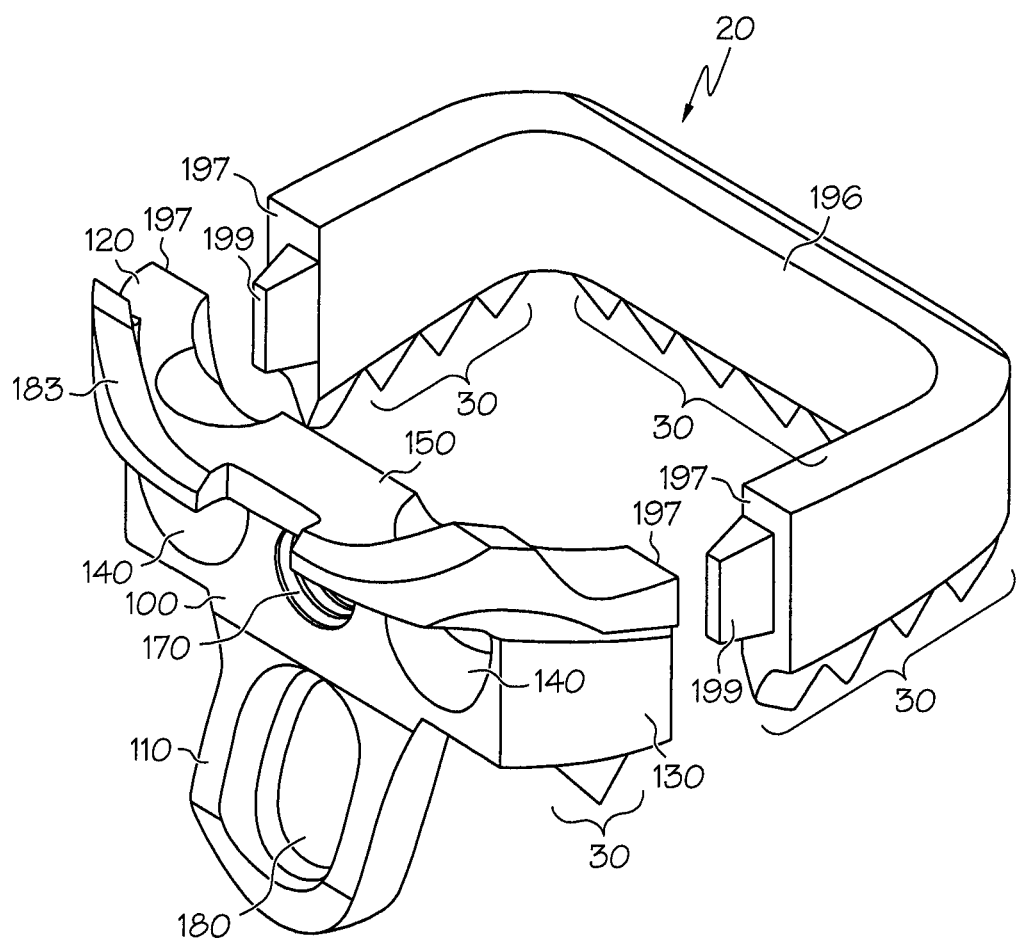
FIG. 6 is an angled front perspective view of a base member of an implant device including a laterally-enclosable chamber in the unassembled position in accordance with an aspect of the present invention.
Figure 7:
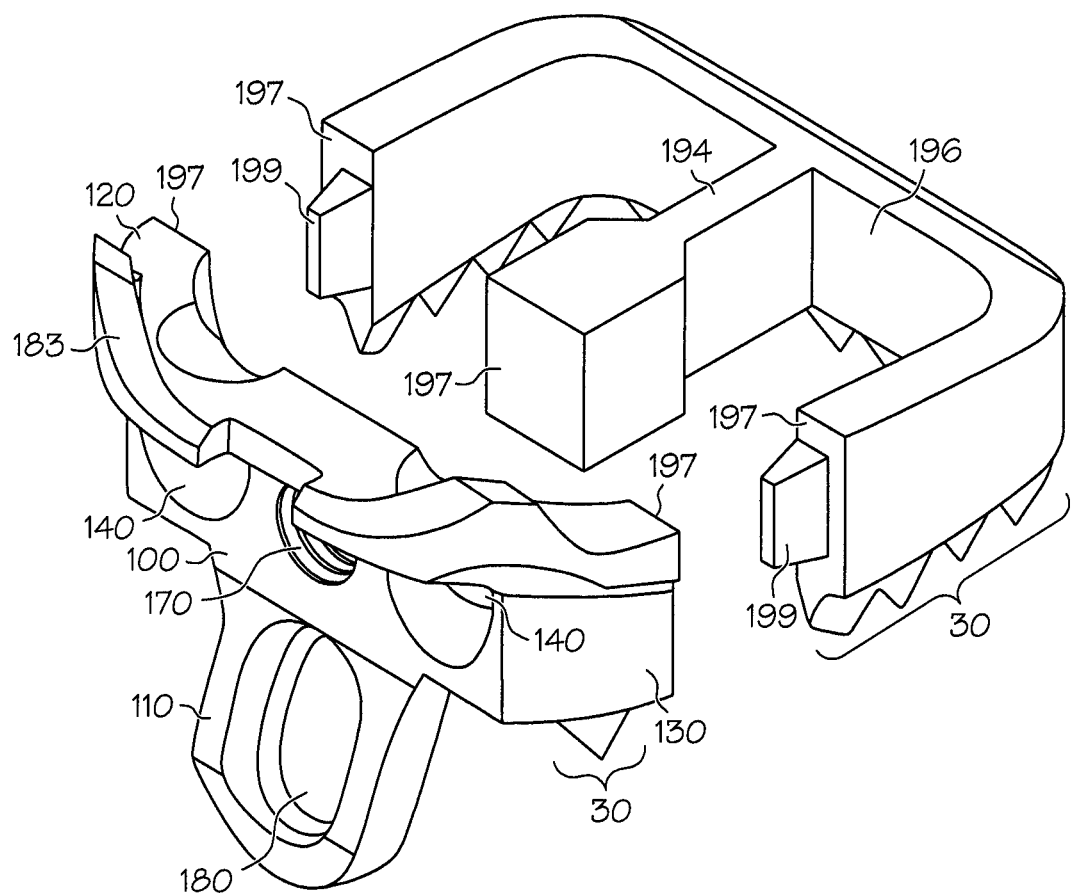
FIG. 7 is an angled front perspective view of a base member of an implant device including a laterally-enclosable, multiple-compartment chamber in an unassembled position in accordance with an aspect of the present invention.

The chamber member 196 can be attached to the primary member 100 in a number of alternative methods. For example, in another embodiment, FIGS. 6 and 7 illustrate a peg and slot system that can be used to secure the chamber member 196 to the primary member 100. The attachment faces 197 of the chamber member 196 can include a peg 199 that corresponds to a slot (not shown) in the attachment faces 197 of the first and second legs 120, 130 of the primary member 100. The slot is of like shape and has dimensions as that of the peg 199 so when fit together the peg 199 and slot are secured tightly. An adhesive that is conventional in the art can also be used to secure the peg 199 and slot together in order to ensure that the chamber member 196 is securely attached to the primary member 100 of the implant device 10.

Figure 8:
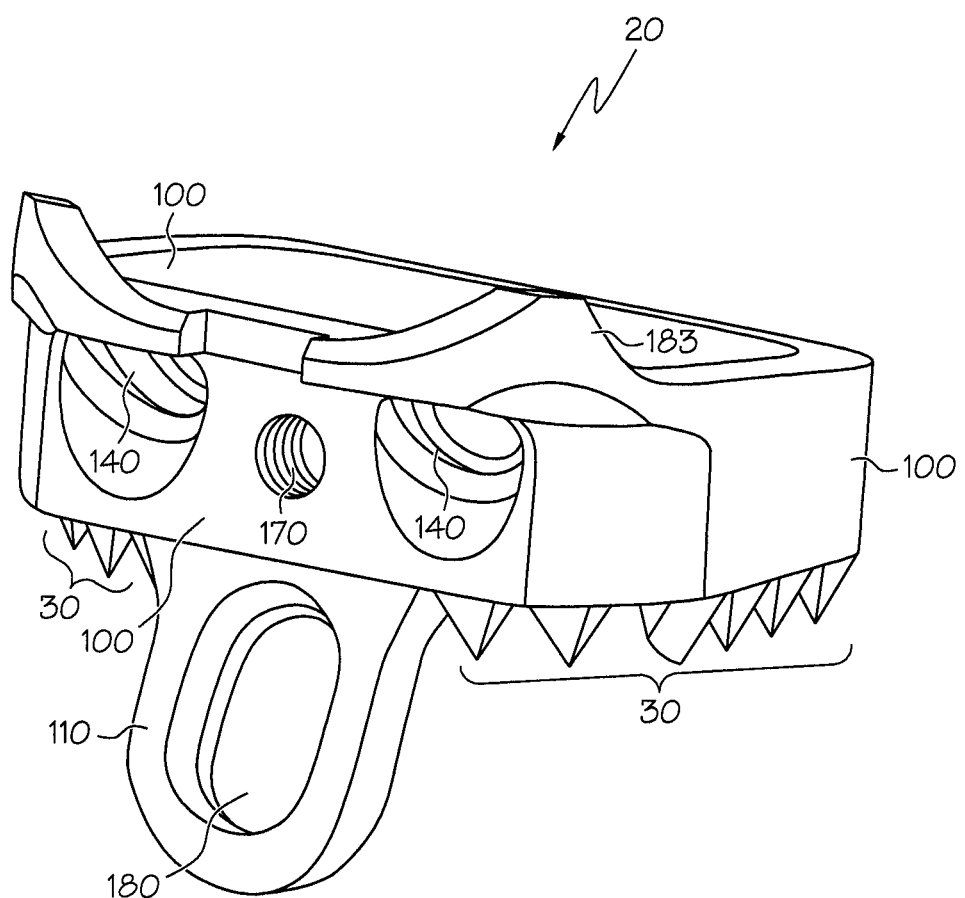
FIG. 8 is a front perspective view of a base member of an implant device including a peripherally-surrounded chamber in accordance with an aspect of the present invention.

In order to address the disadvantage that some radiolucent materials lack the strength of radiopaque materials, design modifications may be required to provide adequate structural integrity to the implant device 10. As illustrated in FIG. 8, the thickness of portions of the primary member 100 and secondary member 110, for example the bone screw holes 140 and slot 180 and portions surrounding the same, can be increased. Increasing the thickness of the bone screw holes 140 and/or slots 180 strengthens and adds support to the interface area between the bone screws 50 that extend into a bone body and the primary and secondary members. Increasing the thickness of these portions likewise will increase the thread length or slot thickness. Designing portions of the implant device 10, such as the primary member 100 and secondary member 110, to be thicker or bulkier than other portions can mitigate the stresses of bone body migration and toggling of the bone screws the forces that may cause the implant device 10 to bend, crack or otherwise be damaged.

It is to be appreciated that the implant device may include various other features. Some of these features may include features set forth within the patent applications identified herein and incorporated herein by reference. Some examples of the feature are shown in FIGS. 9-13. Some of the views are sectioned to show specific details. Such example feature may be utilized within any of the above mentioned embodiments. Of course, the shown features are merely examples and are not to be construed as limitations on the present invention.

Figure 9:
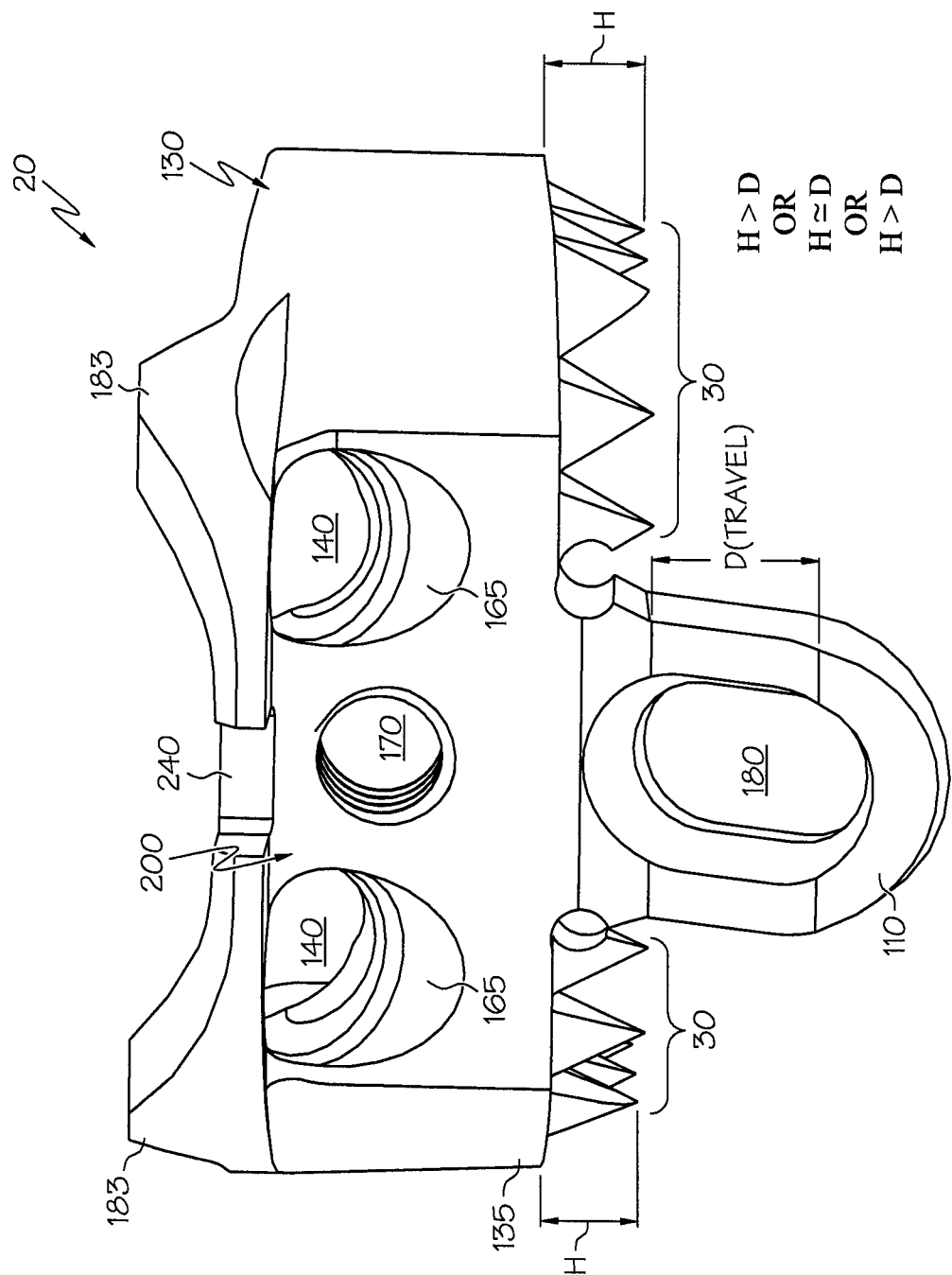
FIG. 9 is a front perspective view of a base member of an implant device illustrating possible modifications to the above-identified embodiments in accordance with an aspect of the present invention.

Turning to FIG. 9, as mentioned, the effective travel height (H) of the interface members 30 relates to a depth of penetration of the interface members into the bone body. However, the height (H) can also have an interrelationship with other relative movements that are associated with the implant device 10. For example, penetration of the interface members 30 into the bone body can be coordinated with pivoting and/or sliding of one or more bone screws relative to their respective holes 140 and slots 180 for controlled subsidence. As shown in FIG. 9, the bone screw associated with the slot can have a travel distance D. In one example concerning relative sliding within the slot 180, as the interface members 30 reach a fully-embedded state, the screw will reach the at the end of the slot 180. Such an example can be generally characterized by considering H to be equal to or approximately equal to D. Thus, the respective bone fastener is located within the slot so the screw travel matches penetration subsidence of the interface members into the bone body.

Other examples concerning relative dimensioning are contemplated. Such other examples include relative sliding travel of the screw within the slot 180 to end before the interface members 30 reach a fully-embedded state and relative sliding travel of the screw within the slot 180 to still be permitted after the interface members 30 reach a fully-embedded state. Such examples can generally be characterized by considering H to be greater than D and by considering H to be less than D, respectively. Also, placement and sliding travel are possible variables. For example, the respective bone fastener can be placed to reach an end of the elongated slot and then toggle in the slot to permit the interface members to further penetrate into the bone body.

Figure 10:
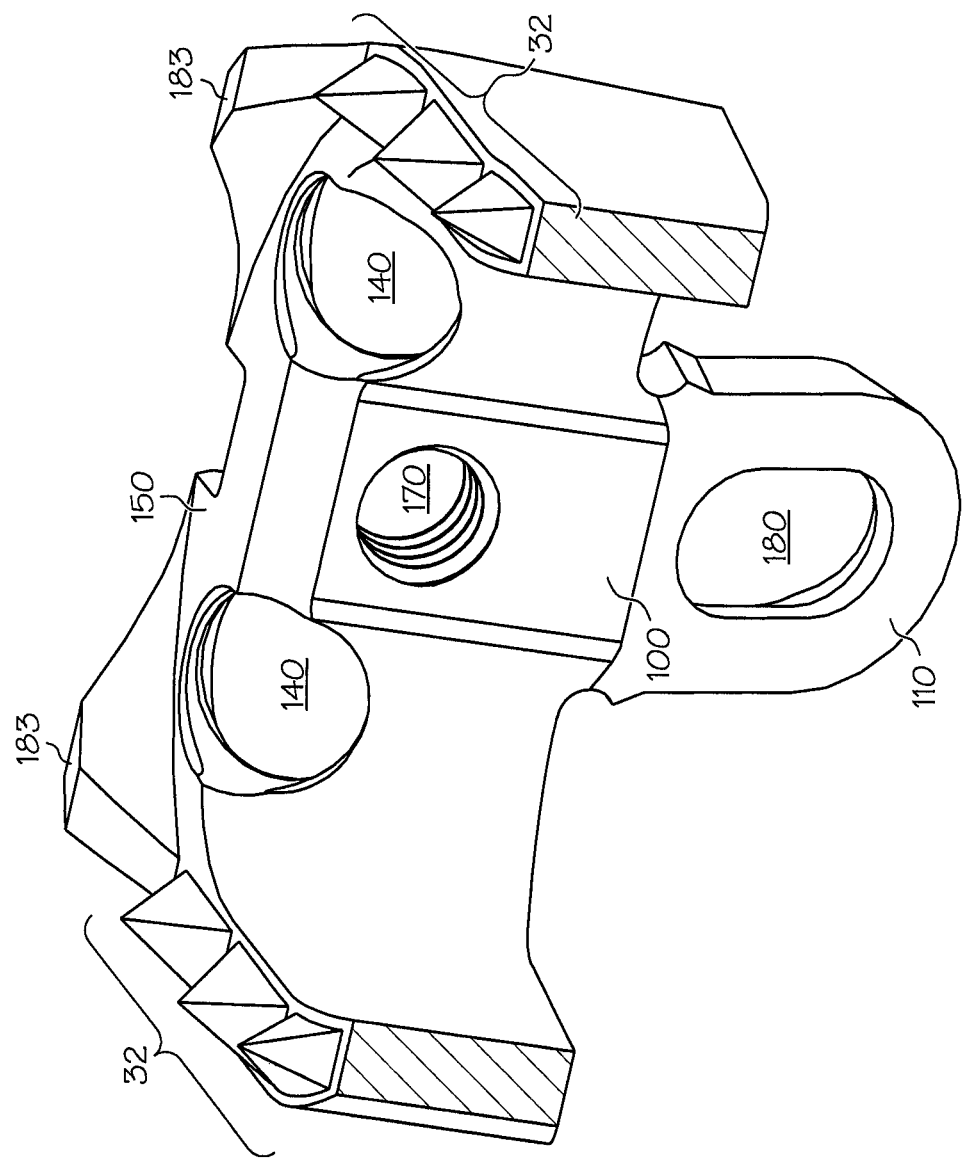
FIG. 10 is partially broken away rear perspective view of a base member of an implant device illustrating possible modifications to the above-identified embodiments in accordance with an aspect of the present invention.
Figure 11:
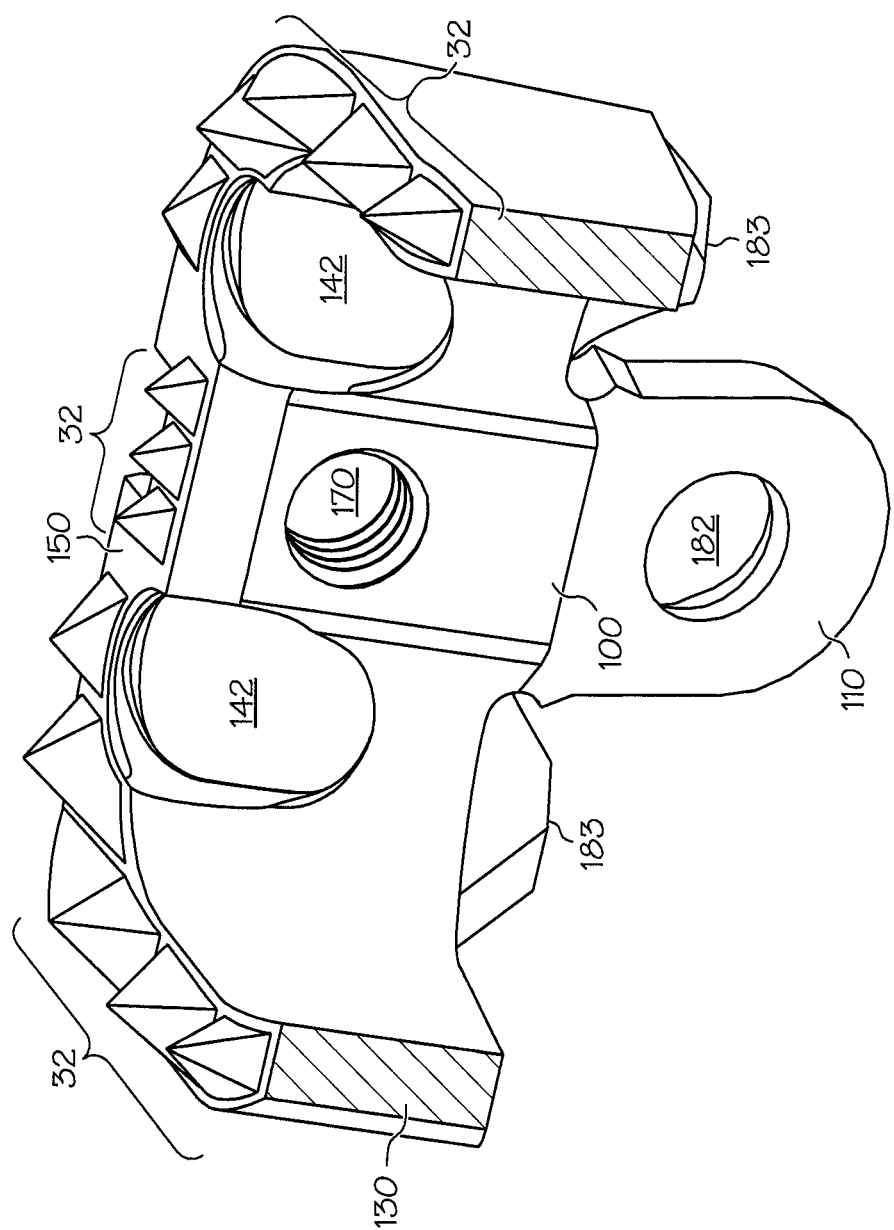
FIG. 11 is partially broken away rear perspective view of a base member of an implant device illustrating possible modifications to the above-identified embodiments in accordance with an aspect of the present invention.

FIG. 10 shows yet another example of another feature. Specifically, the interface members 32 could be located on the top surface. Thus, the location of the interface members is inverted. Another possible inversion relates to the holes and slots. Specifically, FIG. 11 shows the replacement of the holes (140, FIG. 10) with elongate slots 142 (FIG. 11) and replacement of the elongate slot (180, FIG. 10) with a non-elongate hole 182.

Figure 12:
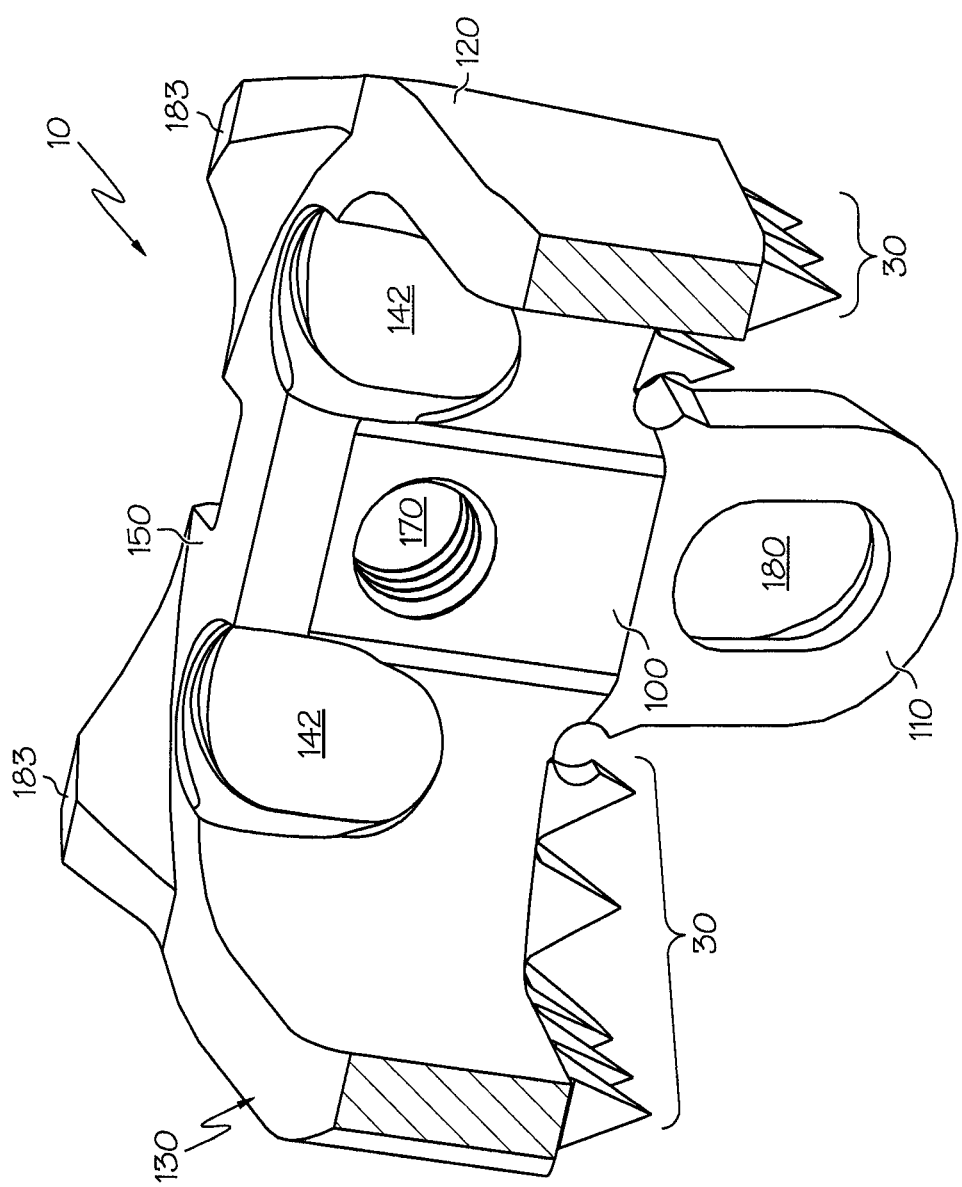
FIG. 12 is partially broken away rear perspective view of a base member of an implant device illustrating possible modifications to the above-identified embodiments in accordance with an aspect of the present invention.
Figure 13:
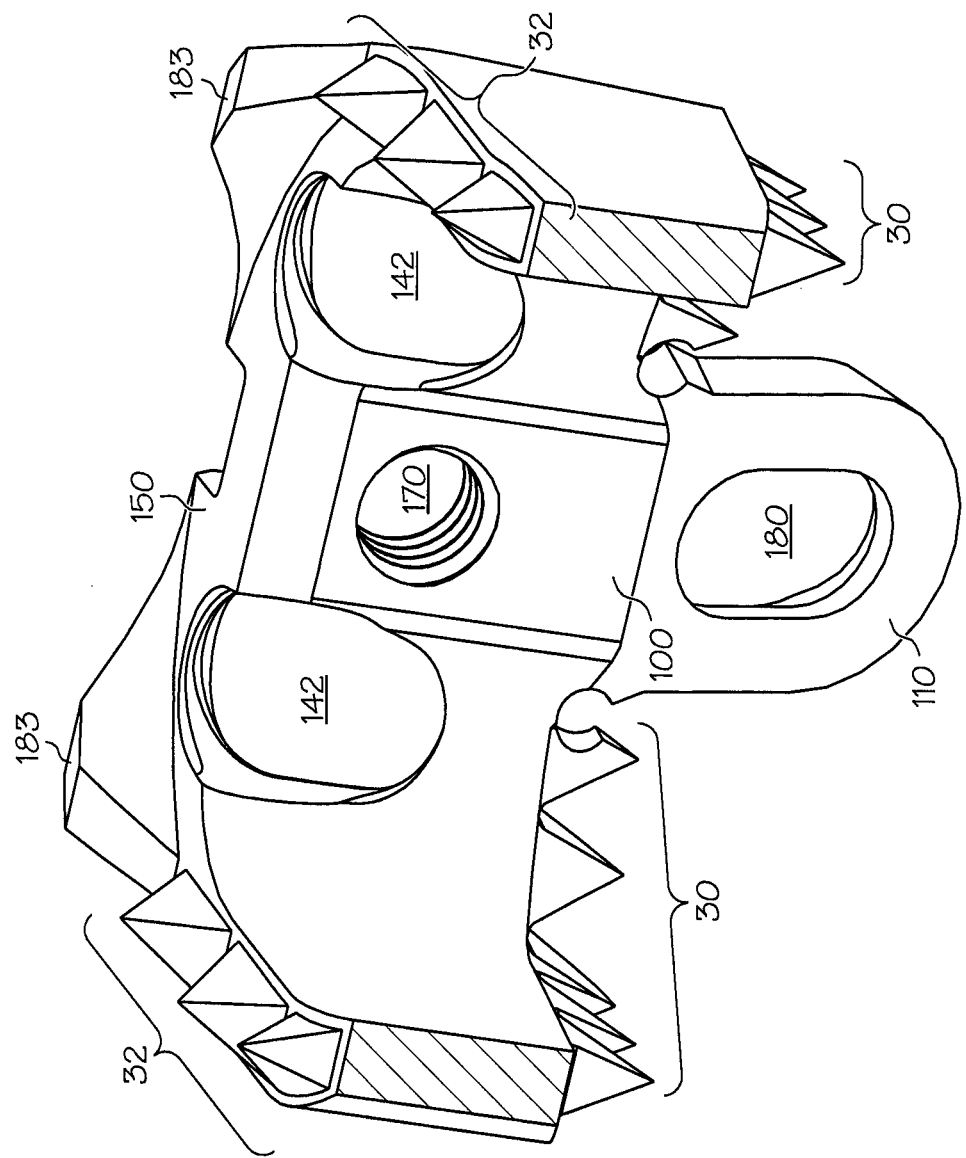
FIG. 13 is partially broken away rear perspective view of a base member of an implant device illustrating possible modifications to the above-identified embodiments in accordance with an aspect of the present invention.

Also, the above-mentioned modifications can be combined within various arrangements. For example, FIG. 12 shows that only slots 142 and 180 are provided. In other words, all holes are modified to slots. As another example, FIG. 13 shows that interface member 30, 32 can be located on both the bottom and top. FIG. 13 also shows the use of only slots 142 and 180. It is to be appreciated that such a combination of interface member 30, 32 and slots 142, 180 can provide for many types of subsidence control. The penetration of interface members and movement along slots can be configured and utilized in many different ways to provide different subsidence profiles. For example, subsidence could require more or less force and or time. Also, the subsidence may have different segments, each with a different profile.

Also, another aspect that can affect the subsidence profile, the interface members 30, 32 can be of any height or combination of heights. Thus, if a plurality of interface members 30, 32 extend from a surface of the base member, each interface member can be of equal heights or substantially taller or shorter than other interface members. FIG. 11 shows interface members 32 that have substantially dissimilar heights depending on the amount of subsidence resistance that is desired. Also, as compared to the interface members on the top and bottom, any relative dimensioning is possible. For example, the height of the interface members extending from the top surface may be greater, about the same, or less than height of the interface members extending from the bottom surface.

Still further, it is contemplated that no relative sliding movement occurs between one, some or all of the plurality of fasteners and the base member during the controlled subsidence. This could be accomplished via use of only holes and no slots. In the alternative, a bone screw could be held against movement along a slot. For such a scenario, pivoting may occur and one of more of the bone screws.

While shown embodiments of the present invention are described for supporting adjacent cervical vertebrae in the anterior region of the vertebrae, persons skilled in the art would recognize that the bone pate of the present invention may be utilized to support adjoining cervical, thoracic and lumbar in the region of the vertebral body. Further, the device and method of the invention is not limited to vertebral bodies, but can also be use to join two other pieces of bone in other parts of the body.

While embodiments and applications of this invention have been shown and described, it would be apparent to those skilled in the art that many more modifications are possible without departing from the inventive concepts herein. The invention, therefore, is not to be restricted except in the spirit of the appended claims.

What is claimed is:

1. An implant device including:
   a base member configured to interface with two or more bone bodies, wherein the base member includes a primary member that forms a peripherally-surrounded bone chamber for receiving fusion material and a secondary member, contiguous with the primary member as part of the base member, that extends at an angle relative to the primary member;
   a plurality of interface members extending from at least one surface of the base member, the interface members being configured to provide controlled subsidence of the implant device into at least one bone body over a period of time subsequent to implantation of the device adjacent to the at least one bone body; and
   a plurality of bone fasteners extending through apertures provided in the base member;
   wherein the peripherally-surrounded chamber for receiving fusion material includes at least two interior compartments.

2. The device of claim 1, wherein a portion of the base member includes a radiolucent material.

3. The device of claim 1, wherein a portion of the base member includes a radiopaque material.

4. The device of claim 1, wherein the primary member has at least one aperture configured to receive a bone fastener there through and the secondary member having at least one aperture configured to receive a bone fastener there through.

5. The device of claim 1, further including restraining cover means for restricting movement of at least one bone fastener extending through an aperture in the base member by covering at least a portion of the at least one bone fastener.

6. The device of claim 1, wherein the primary member includes a detachable chamber member, wherein the detachable chamber member forms a portion of the peripherally-enclosed chamber for receiving fusion material.

7. The device of claim 6, wherein the detachable chamber member includes radiolucent material.

8. The device of claim 6, wherein the primary member further includes a first leg and a second leg that form a curved open area for receiving fusion material when the detachable chamber member is unattached to the primary member.

9. The device of claim 8, wherein the peripherally-surrounded chamber for receiving fusion material is formed when the detachable chamber member is connected to the first leg and the second leg of the primary member.

10. The device of claim 1, wherein the peripherally-surrounded chamber includes a substantially flat inner face surface having an interior member extending from a portion of the inner surface and the interior member being connected to the opposing portion of the inner face surface of the peripherally-surrounded chamber such that the peripherally-surrounded chamber is divided into the at least two interior compartments.

11. The device of claim 1, wherein at least one of the apertures is an elongated slot configured to permit relative travel of the respective bone fastener along the elongation of the slot during the controlled subsidence over a period of time subsequent to implantation of the device.

12. The device of claim 11, wherein the plurality of interface members have a dimensional extension that penetrates into the bone body during the controlled subsidence over a period of time subsequent to implantation of the device, and the respective bone fastener is located within the slot so the screw travel matches penetration subsidence of the plurality of interface members into the bone body.

13. The device of claim 1, wherein at least one of the apertures is an elongated slot, the plurality of interface members have a dimensional extension that penetrates into the bone body during the controlled subsidence over a period of time subsequent to implantation of the device, and the slot having an elongation dimension along which the respective bone fastener moves during the controlled subsidence.

14. The device of claim 13, wherein the dimensional extension of the plurality of interface members is matched to the elongation dimension of the slot such that the respective bone screw reaches an end of the slot as the dimensional extension of the plurality of interface members completes penetration into the bone body.

15. The device of claim 1, wherein relative sliding movement occurs between at least one fastener and the base member during the controlled subsidence over a period of time subsequent to implantation of the device.

16. The device of claim 1, wherein no relative sliding movement occurs between at least one fastener and the base member during the controlled subsidence over a period of time subsequent to implantation of the device.

17. The device of claim 1, wherein no relative sliding movement occurs between the plurality of fasteners and the base member during the controlled subsidence over a period of time subsequent to implantation of the device.

18. The device of claim 1, wherein the controlled subsidence is associated with a dimension of penetration of at least one interface member into the bone body, and at least one bone fastener having a dimension of displacement relative to the base member that is within a range that includes no displacement and also does not include a dimension of displacement that equals the dimension of penetration.

19. The device of claim 1, wherein at least one interface member has a dimension that is fully penetrated into the bone body at some point along the controlled subsidence.

20. The device of claim 19, wherein the at least one interface member is fully penetrated into the bone body at completion of the controlled subsidence.

21. The device of claim 1, wherein relative sliding movement occurs between at least one bone fastener and the base member during the controlled subsidence and the relative sliding is arrested at some point along the controlled subsidence.

22. The device of claim 21, wherein the relative sliding is arrested at completion of the controlled subsidence.

23. The device of claim 1, wherein the plurality of interface members extend from the bottom surface of the primary member.

24. The device of claim 1, wherein at least one of the apertures is an elongated slot that has an elongation length greater than a height of at least one interface member.

25. The device of claim 24, wherein the elongation length of the elongated slot is greater than the height of any single interface member.

26. The device of claim 1, wherein at least one of the apertures is an elongated slot that has an elongation length less than the height of any single interface member.

27. The device of claim 1, wherein at least one of the apertures is an elongated slot and the respective bone fastener is at the end of the elongated slot before at least one interface member is substantially fully penetrated during the controlled subsidence.

28. The device of claim 1, wherein at least one of the apertures is an elongated slot and the respective bone fastener reaches an end of the elongated slot and toggles in the slot to permit the interface members to further penetrate into the bone body.

29. The device of claim 1, wherein at least one aperture in the base member has a generally concave spherical seat to permit the bone fastener extending there through to pivot on the seat and toggle.

30. An implant device including:
a base member configured to interface with two or more bone bodies, wherein the base member includes a primary member that forms a peripherally-surrounded bone chamber for receiving fusion material and a secondary member, contiguous with the primary member as part of the base member, that extends at an angle relative to the primary member;
a plurality of interface members extending from at least one surface of the base member, the interface members being configured to provide controlled subsidence of the implant device into at least one bone body over a period of time subsequent to implantation of the device adjacent to the at least one bone body; and
a plurality of bone fasteners extending through apertures provided in the base member;
wherein the primary member includes a detachable chamber member, wherein the detachable chamber member forms a portion of the peripherally-enclosed chamber for receiving fusion material and wherein the detachable chamber member further includes at least one interior member extending from an inner face surface of the chamber member, and the at least one interior member is configured to divide the peripherally-surrounded chamber for receiving fusion material into at least two interior compartments.

31. The device of claim 30, wherein the at least one interior member includes radiolucent material.

32. An implant device including:
a base member including a peripherally-surrounded chamber for receiving fusion material, wherein the peripherally-surrounded chamber has a top surface and a bottom surface;
a plurality of bone fasteners extending through apertures provided in the base member;
restraining cover means for restricting movement of at least one bone fastener by covering at least a portion of the at least one bone fastener; and
at least one interface member extending from a surface of the peripherally-surrounded chamber, wherein the interface member is configured to provide controlled subsidence of the device into a bone body over a period of time subsequent to implantation of the device adjacent to the bone body;
wherein the peripherally-surrounded chamber includes at least one interior member configured to divide the chamber into at least two interior compartments.

33. The device of claim 32, including a plurality of interface members extending from the surface of the peripherally-surrounded chamber.

34. The device of claim 33, wherein the interface members extend from the bottom surface of the peripherally-surrounded chamber.

35. The device of claim 33, wherein at least one of the apertures is an elongated slot configured to permit relative travel of the respective bone fastener along the slot during the controlled subsidence over a period of time subsequent to implantation of the device, the plurality of interface members have a dimensional extension that penetrates into the bone body during the controlled subsidence, and the respective bone fastener is located within the slot so the screw travel matches penetration subsidence of the plurality of interface members into the bone body.

36. The device of claim 33, wherein the controlled subsidence is associated with a dimension of penetration of at least one interface member into the bone body, and at least one bone fastener having a dimension of displacement relative to the base member that is within a range that includes no displacement and also does not include a dimension of displacement that equals the dimension of penetration.

37. The device of claim 32, wherein a portion of the base member includes a radiolucent material.

38. The device of claim 32, wherein a portion of the base member includes a radiopaque material.

39. An implant device including:
a base member configured to interface with first and second adjacent bone bodies, the base member includes a primary member that forms a peripherally-surrounded bone chamber for receiving fusion material and configured such that the first and second bone bodies engage the fusion material for permitting force transmission between the first and second bone bodies through the fusion material, the base member having a plurality of bone fastener receiving apertures extending there through;
a plurality of bone fasteners extending through the apertures in the base member; and
means for controlled subsidence of movement of the first and second bone bodies toward each other over a period of time subsequent to implantation of the device interposed between the first and second bone bodies;
wherein the peripherally-surrounded chamber for receiving fusion material includes at least two interior compartments.

40. The device of claim 39, wherein the means for controlled subsidence of movement include a plurality of interface members extending from at least one surface of the base member, the interface members being configured to provide controlled subsidence of the implant device into at least one bone body.

41. The device of claim 39, wherein a portion of the base member includes a radiolucent material.

42. The device of claim 39, wherein a portion of the base member includes a radiopaque material.

43. The device of claim 39, wherein the primary member includes a detachable chamber member, wherein the detachable chamber member forms a portion of the peripherally-enclosed chamber for receiving fusion material.

44. The device of claim 43, wherein the detachable chamber member includes radiolucent material.

45. The device of claim 43, wherein the primary member further includes a first leg and a second leg that form a curved open area for receiving fusion material when the detachable chamber member is unattached to the primary member.

46. The device of claim 45, wherein the peripherally-surrounded chamber for receiving fusion material is formed when the detachable chamber member is connected to the first leg and the second leg of the primary member.

47. The device of claim 39, wherein the peripherally-surrounded chamber includes a substantially flat inner face surface having an interior member extending from a portion of the inner surface and the interior member being connected to the opposing portion of the inner face surface of the peripherally-surrounded chamber such that the peripherally-surrounded chamber is divided into the at least two interior compartments.

48. The device of claim 39, further including restraining means for restricting movement of at least one bone fastener.

49. The device of claim 48, wherein the restraining means includes a cover extending over a portion of at least one bone fastener for preventing back-out of the bone fastener.

50. An implant device including:
a base member configured to interface with first and second adjacent bone bodies, the base member includes a primary member that forms a peripherally-surrounded bone chamber for receiving fusion material and configured such that the first and second bone bodies engage the fusion material for permitting force transmission between the first and second bone bodies through the fusion material, the base member having a plurality of bone fastener receiving apertures extending there through;
a plurality of bone fasteners extending through the apertures in the base member; and
means for controlled subsidence of movement of the first and second bone bodies toward each other over a period of time subsequent to implantation of the device interposed between the first and second bone bodies;
wherein the primary member includes a detachable chamber member, wherein the detachable chamber member forms a portion of the peripherally-enclosed chamber for receiving fusion material and wherein the detachable chamber member further includes at least one interior member extending from an inner face surface of the chamber member, wherein the at least one interior member is configured to divide the peripherally-surrounded chamber for receiving fusion material into at least two interior compartments.

\* \* \* \* \*